(12) United States Patent
Geva et al.

(10) Patent No.: US 6,466,806 B1
(45) Date of Patent: Oct. 15, 2002

(54) PHOTOACOUSTIC MATERIAL ANALYSIS

(75) Inventors: Jacob Geva, Rishon Le Zion; Leonid Trachtenberg, Rishon Lezion; Anatoly Kravetz, Ness Ziona, all of (IL)

(73) Assignee: Card Guard Scientific Survival Ltd., Rehovot (IL)

( * ) Notice: Subject to any disclaimer, the term of this patent is extended or adjusted under 35 U.S.C. 154(b) by 0 days.

(21) Appl. No.: 09/573,528

(22) Filed: May 17, 2000

(51) Int. Cl.$^7$ ............................................. A61B 5/00
(52) U.S. Cl. .................... 600/310; 600/322; 600/473
(58) Field of Search .................... 600/309–310, 600/322–324, 316, 336, 473, 476; 374/45; 356/39–42

(56) References Cited

U.S. PATENT DOCUMENTS

| | | | | |
|---|---|---|---|---|
| 3,749,476 A | * | 7/1973 | Daley et al. | 359/286 |
| 4,484,820 A | * | 11/1984 | Rosencwaig | 374/6 |
| 4,833,333 A | * | 5/1989 | Rand | 250/492.3 |
| 5,085,080 A | * | 2/1992 | Yu | 73/579 |
| 5,348,002 A | * | 9/1994 | Caro | 600/310 |
| 5,941,821 A | | 8/1999 | Chou | |
| 6,049,728 A | | 4/2000 | Chou | |
| 6,219,575 B1 | * | 4/2001 | Nemati | 604/20 |

OTHER PUBLICATIONS

A.N. Kravets, S. A. Kravets, "Yag: Nd Laser System with Parallel Connection of Active Elements and Passive Q–Switching", Kovrov Institute of Technology, SPIE vol. 2713, pp. 124–129, Russia.

A. N. Kravets, S. A. Kravets, I.I. Trifonov, "Phase Conjugated Laser System with Parallel Connection of Active Elements", Kovrov Institute of Technology, SPIE vol. 2771 pp. 88–94, Russia.

A. N. Kravets, T.T. Basiev, S. B. Mirob, A. V. Fedin, "Technological Nd–Laser with Passive Q–Switches Based on LiF:$F_2$ Crystals". Kovrov Institute of Technology, SPIE vol. 1839 Solid State Laser And New Laser Materials (1991), pp. 2–11, Russia.

A. N. Kravets, I.N. Kompanets, S. I. Trifonova, "Technological Nd–Lasers with Q–Switching and their Applications", P. N. Lebedev Physical Institute, Russian Academy of Sciences, SPIE vol. 2062, pp. 159–166.

\* cited by examiner

*Primary Examiner*—Eric F. Winakur
*Assistant Examiner*—Matthew Kremer
(74) *Attorney, Agent, or Firm*—Eitan, Pearl, Latzer & Cohen-Zedek

(57) ABSTRACT

Disclosed is a method and apparatus for determining the concentration of an interest component in a medium by resonant photoacoustic spectroscopy (RPAS) with a light pulse-train comprising equidistant short pulses having variable duration, frequency, number, and power. The light wavelength is selected so as to be absorbed by the component of interest. Upon irradiation, acoustic oscillations are generated by the absorbed light in a relatively thin layer of the medium, characterized by a heat-diffusing length. The frequency repetition of the light short pulses in the pulse-train is chosen equal to the natural acoustic oscillation frequency of the thin layer of the medium that can be considered as a thin membrane. So, the acoustic oscillation becomes resonant. Measuring of the amplitude and the frequency of the resonant oscillations determine the concentration of interest component. The method and apparatus are suitable monitoring of blood components, especially glucose.

23 Claims, 2 Drawing Sheets

PHOTOACOUSTIC MATERIAL ANALYSIS

FIELD OF THE INVENTION

The present invention relates to electro-optics in general, and more particularly to photoacoustic material analysis.

BACKGROUND OF THE INVENTION

Conventional methods of material analysis such as absorption and luminescent spectroscopy, Raman spectroscopy, and measuring polarization and reflectance changes are not sufficiently suitable for a turbid medium such as human tissue due to significant diffuse scattering of the reference light beam. As an alternative, other material analysis techniques employ photoacoustic spectroscopy, in which a laser beam is used to rapidly heat a sample generating an acoustic pressure wave that can be measured by high-sensitivity ultrasonic detectors such as piezo-electric crystals, microphones, optical fiber sensors, laser interferometers or diffraction sensors.

The laser radiation wavelength is selected so as to be absorbed by the interest component in the medium being analyzed, Thus, laser excitation of a medium is used to generate an acoustic response and a spectrum as the laser is tuned. The use of photoacoustic spectroscopy for glucose testing in blood and human tissue can provide greater sensitivity than conventional spectroscopy. An excellent correlation between the photo-acoustic signal and blood glucose levels has been demonstrated on index fingers of both healthy and diabetic patients.

A prior art method and apparatus for noninvasive measurement of blood glucose by photo-acoustic techniques is described in U.S. Pat. Nos. 5,941,821 and 6,049,728, in which an excitation source provides electromagnetic energy at a wavelength corresponding to the absorption characteristics of the analysis. Upon irradiation, acoustic energy is generated in a relatively thin layer of the sample to be measured, characterized by a heat-diffusing length. The acoustic emission is detected with a differential microphone, one end of which is positioned in a measuring cell and the other end of which is positioned in a reference cell. A processor determines the concentration of the substance being measured based upon the detected acoustic signal. In order to determine the concentration of glucose in the bloodstream, the excitation source is preferably tuned to the absorption bands of glucose in spectral ranges from about 1520–1850 nm and about 2050–2340 nm to induce a strong photo-acoustic emission. In these wavelength ranges, water absorption is relatively weak and glucose absorption is relatively strong. Thus, even though tissue may have a high percentage of water at the above-specified wavelength ranges, the electromagnetic radiation is able to penetrate through the tissue to a sufficient depth to allow for accurate measurements. Despite water absorption, the acoustic signal which is generated by the absorption of electromagnetic radiation by glucose is not overwhelmed by that generated by water. The glucose optically absorbs the energy inducing a temperature rise and generating an acoustic emission indirectly in the air. Thus, the photo-acoustic intensity is approximately linearly proportional to the glucose concentration.

Unfortunately, prior art photo-acoustic material analysis techniques are disadvantageous in that they teach the application of energy to a medium without giving consideration to its acoustic oscillation properties, thus requiring relatively high laser power. Consequently, such techniques are energy inefficient, and provide an inadequate level of sensitivity.

SUMMARY OF THE INVENTION

The primary object of the present invention is to provide a novel method and apparatus of resonant photoacoustic spectroscopy (RPAS) for material analysis that is suitable for determining a concentration of an interest component in a medium. The method comprises irradiating a surface of the medium having the interest component with a light pulse-train comprising equidistant short pulses having variable duration, frequency, number, and power. The frequency of the light short pulses is chosen equal to a natural acoustic oscillation frequency in a medium for resonant light-excitation of acoustic modes. The wavelength of the light pulses is selected so as to excite resonant acoustic oscillation in the medium due to absorption of light by the interest component and subsequent adiabatic temperature rise in the testing area of the medium.

Another object of the present invention is to provide a novel method and apparatus for determination of the concentration of an interest component in the medium like human tissue. A pulsed laser beam generates acoustic oscillations in the dermal or epidermal area of the skin that can be considered as a thin membrane. The membrane has the natural frequencies of acoustic oscillations that depend on the elastic constants of the membrane and its thickness and square. According to the present invention, if the frequency repetition of the light short pulses in the pulse-train equals the natural oscillation frequency of the membrane, resonance of acoustic oscillations results. The amplitude and frequency of the resonant acoustic oscillations depend on the concentration of interest component in the human tissue due to absorption of light with a predetermined wavelength. The concentration is determined in response to electrical signals of a detector of the resonant acoustic oscillations exciting in the medium. The present invention is suitable for measuring blood components in human tissue, especially glucose.

A further object of the present invention is to provide a novel type of the Q-switched laser device for material analysis, which is suitable for noninvasive blood glucose monitoring, based on the RPAS as disclosed herein. The laser device is preferably a solid-state laser with an unstable resonator and passive Q-switch (PQS) on colored LiF crystal. The transparency of the PQS changes linearly with crystal length that provides pulse-train generation giving equidistant short pulses having variable duration, frequency, number and power. It is possible to optimize frequency and energy of laser radiation by moving the PQS to a position perpendicular to the optical axis of the laser cavity.

BRIEF DESCRIPTION OF THE DRAWINGS

The present invention will be understood and appreciated more fully from the following detailed description taken in conjunction with the appended drawings in which.

DETAILED DESCRIPTION OF PREFERRED EMBODIMENTS

Figure 1:
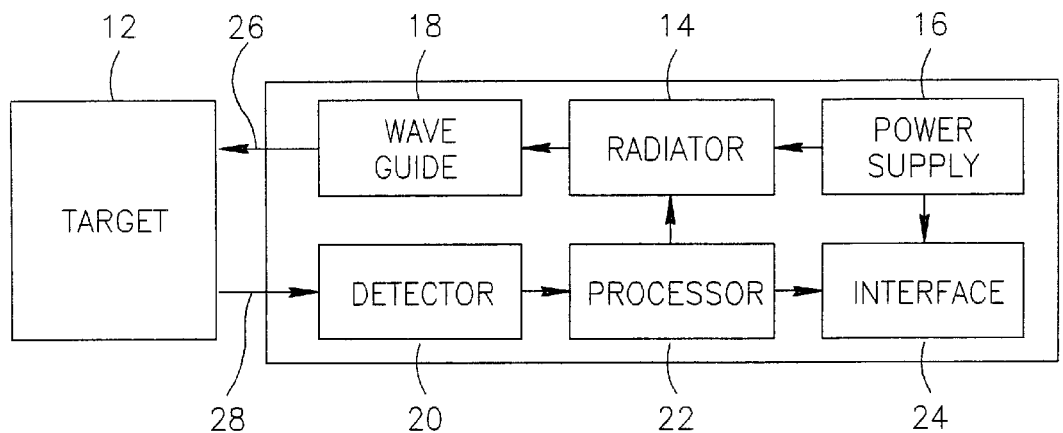
FIG. 1 is a simplified block diagram of an electronic-optical apparatus, constructed and operative in accordance with a preferred embodiment of the present invention.

Reference is now made to FIG. 1, is a simplified block diagram of an electronic-optical apparatus, constructed and operative in accordance with a preferred embodiment of the present invention. Electronic-optical apparatus 10 is provided for delivering a laser beam 26 to a target 12 in such a manner that laser beam 26 is directed toward a desired portion of target 12. Electronic-optical apparatus 10 preferably comprises a radiator 14, typically a diode laser or a solid-state laser, powered by a power supply 16. Radiator 14 preferably provides pulse-train generation giving equidistant short laser pulses having variable duration, frequency, number and power. Laser beam 26 is preferably passed through an optical wave-guide 18, typically an optical fiber, which is used to inject laser beam 26 into target 12. The pulse-periodic electromagnetic radiation of radiator 14 excites target 12 to produce acoustic oscillations 28.

An acoustic detector 20, typically a microphone or an optical fiber sensor, detects acoustic oscillations 28 from target 12. A lock-in amplifier (not shown) may be optionally used to increase the electrical signals from detector 20. A processor 22 preferably calculates the concentration of a component of interest in target 12, such as glucose, in accordance with techniques described in greater detail hereinbelow. Processor 22 may be any suitable processor or microprocessor, and may implement conventional frequency domain analysis techniques to analyze the temporal frequency response of the extracted acoustic signal in order to improve the signal-to-noise ratio. Conventional chromometric spectral analysis techniques may also be utilized to deduce the observed photo-acoustic spectrum in order to improve the detection limit and accuracy. An electronic interface 24 is preferably provided to control the operation of radiator 14 and power supply 16 to generate a pulse-train light beam comprising equidistant short pulses with variable duration, frequency, number and power in response to the level of the acoustic signal output from detector 20.

Figure 2:
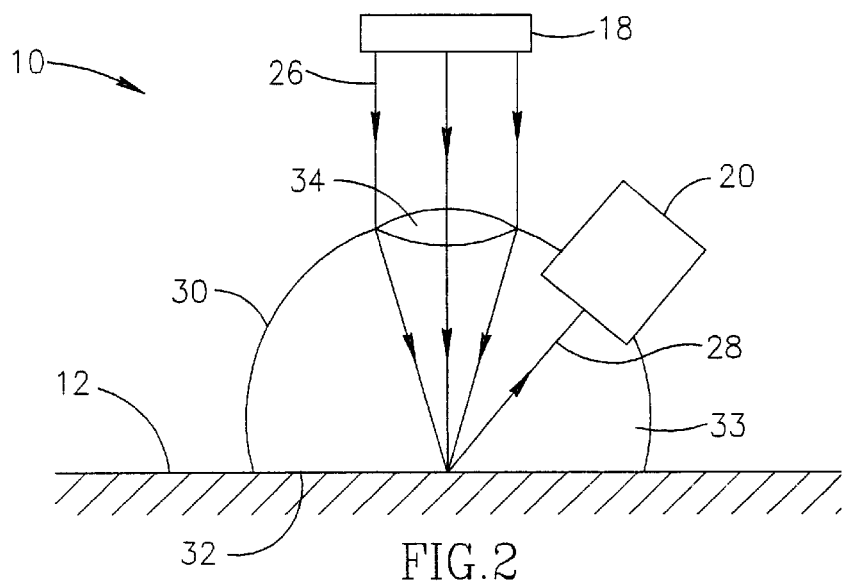
FIG. 2 is a simplified, cross-sectional view of an implementation of the apparatus of FIG. 1, constructed and operative in accordance with a preferred embodiment of the present invention.

Reference is now made to FIG. 2, which is a simplified, cross-sectional view of an implementation of the apparatus of FIG. 1, constructed and operative in accordance with a preferred embodiment of the present invention. In the implementation of FIG. 2 the apparatus of FIG. 1 is preferably arranged such that laser beam 26 is injected by wave guide 18 into the interior of an acoustic cell 30. Acoustic cell 30 may be constricted from any suitable material, preferably ABS plastic material. Acoustic cell 30 transmits the acoustic oscillations 28 from target testing area 32 to acoustic detector 20 via air. Acoustic cell 30 preferably acts as a housing for acoustic detector 20 and a convex lens 34. Acoustic cell 30 is designed to be positioned on the surface of a target testing area 32 of target 12, such as human skin, and has an aperture 33 to permit laser light to be applied to the testing area. Convex lens 34 serves to focus laser beam 26 onto the plane of target testing area 32. Acoustic detector 20 then detects the acoustic oscillations 28 from target testing area 32 with acoustic cell 30.

Where the component of interest being tested is glucose and the target is human skin, the glucose optically absorbs the light energy of laser beam 26, thereby inducing an adiabatic temperature rise in target testing area 32 and generating acoustic oscillations 28 indirectly in air. The acoustic wave spectrum depends on the glucose concentration in the interstitial fluid (ISF) that surrounds the cells within the tissue. Glucose levels in ISF are about 10% lower than glucose levels in blood.

The dermal or epidermal area of the skin that generates acoustic waves can be considered as a thin membrane. The membrane has natural oscillation frequencies that depend on the thickness of the membrane, its elastic constants, and the square of the membrane surface that is equal to the square of the aperture 33.

According to the present invention, if the repetition frequency of the light pulses causing the acoustic oscillations equals the oscillation frequency of the membrane, the oscillation becomes resonant. Under such circumstances the amplitude of the oscillations increases many times, increasing the signal-to-noise ratio and, thus, testing sensitivity.

Figure 3:
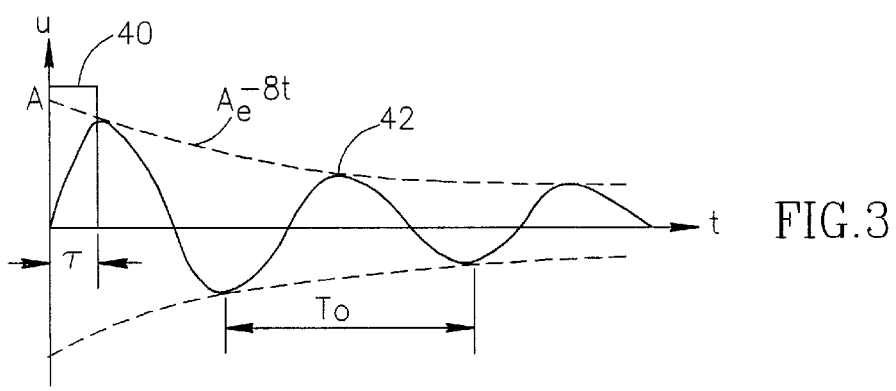
FIG. 3 is a simplified graphical illustration of acoustic oscillations of a medium upon which short mono-pulse laser-excitation has been applied in accordance with a preferred embodiment of the present invention.

Reference is now made to FIG. 3, which is a simplified graphical illustration of acoustic oscillations of a medium upon which short mono-pulse laser-excitation has been applied in accordance with a preferred embodiment of the present invention. In the graph of FIG. 3, if the duration $\tau$ of the short laser pulse 40 is much less than the period $T_0$ of the oscillations 42 of the target membrane, the oscillations will be damping. In this case, displacement of the membrane is $$U(t) = A e^{-\delta t} \sin(\omega t - \phi) \tag{EQ. 1}$$

where A is the primary amplitude, $\delta$ is damping coefficient, $\omega$ is circular frequency, and $\phi$ is the primary phase.

During the photo-acoustic effect, a laser light upon absorption induces an adiabatic temperature rise resulting in a pressure build-up, followed by an acoustic shock wave propagating to the surface. The product of the absorption coefficient and local fluence rate, as well as thermophysical properties of the medium determine the amplitude of the generated photo-acoustic signal. The light path of the photon as it is scattered before being absorbed is therefore not relevant. Ultrasonic transduction is preferably used for detection of acoustic oscillations of the surface.

The photo-acoustic signal, expressed as a pressure, is determined by the thermo-elastic expansion coefficient, $\beta$, optical absorption coefficient, $\mu$, and distribution of the absorbed photons H(z) as follows:

$$P(z) = \beta^2 H(z) \mu / C_p, \tag{EQ. 2}$$

where z is depth, and $C_p$ is heat capacity at constant pressure of the medium.

According to Beer's law, the optical absorption coefficient, and consequently the photo-acoustic signal, is proportionate to the concentration of the component of interest in the medium being tested.

EQ. 2 is strictly valid only when the heating process is instantaneous compared to the medium expansion resulting in instant stress generation. Temporal stress confinement requires laser pulse durations that are much shorter than the time propagation across the light penetration depth in the medium. Laser pulses with a duration of several nanoseconds are an ideal light source for excitation of acoustic oscillations in human tissue.

Figure 4:
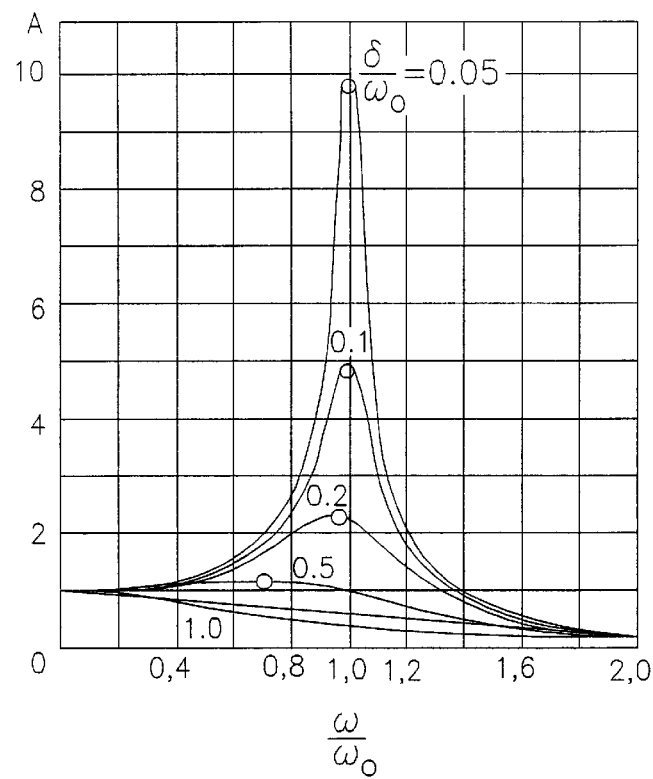
FIG. 4 is a simplified graphical illustration of resonant curves caused by pulse-train laser-excitation in accordance with a preferred embodiment of the present invention.

Reference is now made to FIG. 4, which is a simplified graphical illustration of resonant curves caused by pulse-train laser-excitation in accordance with a preferred embodiment of the present invention. As shown in FIG. 4, the frequency $\omega$ of the short pulses in the pulse-train equals the oscillation frequency $\omega_0$ of a medium for different damping coefficients $\delta$. It may thus be seen from FIG. 4 that a desirable resonant condition may be expressed by the equation:

$$\delta/\omega_0 < 0.1 \qquad (EQ.\ 3)$$

Figure 5:
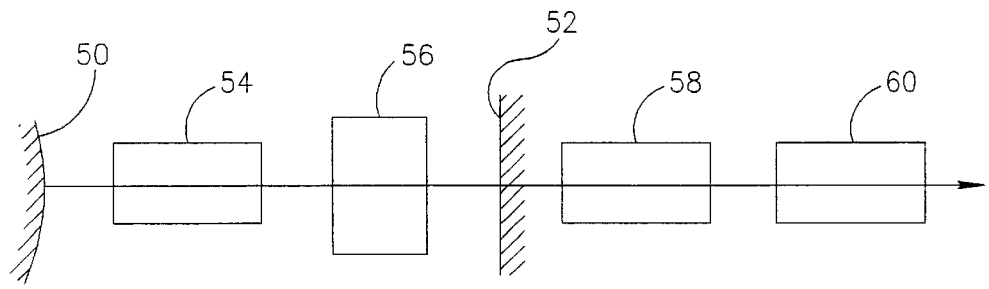
FIG. 5 is a simplified block diagram of a cavity of a Q-switched solid-state laser. constructed and operative in accordance with a preferred embodiment of the present invention.

Reference is now made to FIG. 5, which is a simplified block diagram of a cavity of a Q-switched solid-state laser, constructed and operative in accordance with a preferred embodiment of the present invention. The laser cavity shown in FIG. 5 may form part of the radiator 14 of FIG. 1. The laser cavity comprises an unstable optical resonator, which is preferably formed by a convex end mirror 50 and a flat output mirror 52.

An active optical media 54 is preferably located within the cavity between mirrors 50 and 52. The optical media is preferably an Er-glass or $Co:MgF_2$ for noninvasive blood glucose testing. Alternative optical media may include a neodymium-containing medium, such as, but not limited to, Nd:YAG, Nd:YLF, Nd:YVO$_4$, Nd:SGGM, Cr-Nd:GSGG, Nd-glass. The optically active medium 54 of a solid-state laser maybe crystal or glass having rod or slab shapes. A flash arc lamp or laser diode arrays may be used for optical pumping of the active medium 54.

The laser cavity also preferably includes an active or passive Q-switch medium 56 disposed between the active optical medium 54 and the output mirror 52. Where Q-switch medium 56 is active, acousto-optic modulator may be used. Where Q-switch 56 is passive (PQS), it is preferably made of $LiF:F_2^-$ crystals, these being able to withstand high laser energies than different materials. Such a PQS has several advantages, when used with Nd-containing active laser media, over electro-optical or acousto-optical switches. For example, it does not require external electrical energy. It also has advantages over organic dyes, including higher thermo-optical stability, modulation efficiency, compactness, and low cost. Its modulation efficiency is higher than that of $YAC:Cr_4^+$ crystals. LiF crystals also have color centers that are useful for passively Q-switching alexandrite and ruby laser active media.

It is possible to optimize Q-switching frequency and energy by moving the PQS 56 to a position perpendicular to the optical axis of the cavity if the transparency of the PQS changes linearly with crystal length. The PQS can thus provide a novel type of solid-state laser that radiates pulse-trains. The pulse-train preferably consists of equidistant short pulses with variable duration of between 10 ns and 500 ns, and variable numbers of short pulses in the train, between 1 and 1000 pulses, having a frequency of up to 1 MHz and up to 1 MW of radiation power.

The unstable cavity, in conjunction with convex mirror 50, allows a beam to be obtained which is single-mode and of high spatial brightness, small divergence and high coherence. The radius of curvature of the mirror 50 and its position within the cavity determine the quality of the beam.

High beam quality may be achieved as a result of compensation of the thermal lens that is induced in the active media 54 due to heating inside the cavity. In this case the thermal lens in the active media 54 and the convex mirror form a telescope which satisfies the equation:

$$F = R + C + h, \qquad (EQ.\ 4)$$

where F is focal length of the thermal lens induced in the active media 54, R is radius of curvature of the convex mirror 50, C is distance between the convex mirror 50 and the front of the active media 54, $h = \frac{1}{2}n$ is distance between the front of the active media 54 and the main plane of thermal lens, l is length of the active media 54, and n is the refractive index of the active media 54.

The efficacy of the laser for material analysis is highly dependent on the characteristics of the beam in terms of light amplitude distribution, mode of operation, width of fundamental pulse, instantaneous power within the pulse, wavelength, fine-tuning, and ability to change these and other beam parameters. An amplification active media 58 and an optical converter 60 is preferably provided within the optical cavity and beyond the output mirror 52 to increase the output capabilities of the laser. The optical converter 60 serves to convert the radiation wavelength of the active media 54 to another wavelength, and thus double harmonic generation can be obtained using different nonlinear crystals such as KTP, BBQ, and LBO.

Optical converter 60 may be a dye-impregnated polymer rod or slab, and is preferably operable to convert the green double harmonic into red or orange (i.e., longer wavelength) radiation. Optical converter 60 may also include a dichroic mirror to separate the different wavelength of the radiation. Other kinds of optical converters include various active laser media such as Ti:sapphire, alexandrite, and ruby, which may be pumped by the aforementioned double harmonic radiation to provide radiation of the longer wavelength required.

Where an Nd:YAG laser is used, it is preferably arranged to radiate 1064 nm or 1320 nm wavelength. Thus, a $Co:MgF_2$ crystal may be used as the optical converter 60 by pumping at a wavelength of 1320 nm to provide tuning radiation in the spectral range of 1750–2500 nm.

Other nonlinear crystals may be used to provide third and fourth harmonics, in the blue and ultra-violet regions respectively, or to provide optical parametric oscillation (OPO), in accordance with conventional techniques.

High efficiency wavelength conversion between 266 nm and 5 $\mu$m is thus realized due to high spatial brightness and low divergence of the single-mode radiation.

While the methods and apparatus disclosed herein may or may not have been described with reference to specific hardware or software, the methods and apparatus have been described in a manner sufficient to enable persons of ordinary skill in the art to readily adapt commercially available hardware and software as may be needed to reduce any of the embodiments of the present invention to practice without undue experimentation and using conventional techniques.

While the present invention has been described with reference to a few specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

What is claimed is:

1. Apparatus for determination of an interest component in a human body, comprising:

at least one light source operative to emit a light pulse-train comprising equidistant short pulses with variable in the frequency, duration, number and power output to excite resonant acoustic oscillations in said human body;

a detector for detecting said resonant acoustic oscillations and generating an electrical signal representative of the amplitude and resonant frequency of said resonant acoustic oscillations; and a processor for determining the concentration of said component in response to said electrical signal.

2. Apparatus according to claim 1 wherein said light source is operable to emit said short light pulses with a predetermined wavelength for exciting of said resonant acoustic oscillation in said human body due to absorption of light by said component and subsequent adiabatic temperature rise in a testing area of said human body.

3. Apparatus according to claim 1 wherein said light source is a pulsed laser.

4. Apparatus according to claim 1 wherein said light source is a neodymium containing medium laser.

5. Apparatus according to claim 1 wherein said light source is an Erbium-doped fiber laser for noninvasive blood glucose monitoring.

6. Apparatus according to claim 1 wherein said light source is an Er-glass rod or slab laser with pumping by diode lasers or flash lamp.

7. Apparatus according to claim 1 wherein said light source is a tunable $Co:MaF_2$ laser.

8. Apparatus according to claim 1 and further comprising a Q-switch located within an optical resonator of said light source.

9. Apparatus according to claim 8 wherein said Q-switch is a LiF crystal with color centers.

10. Apparatus according to either of claim 8 or claim 9 wherein said Q-switch provides pulse-train generation giving equidistant short pulses having variable duration, frequency, number and power.

11. Apparatus according to claim 1 and further comprising an optical converter for converting the wavelength of said light source.

12. Apparatus according to claim 1 wherein said light source is a tunable diode laser.

13. Apparatus according to claim 12 further comprising an optical fiber amplifier to increase the output capabilities of the laser.

14. Apparatus according to claim 1 wherein said light source is a fiber coupled diode laser array.

15. Apparatus according to claim 1 wherein said detector of said resonant acoustic oscillations is a microphone.

16. Apparatus according to claim 1 further comprising a measuring acoustic cell adapted to enclose to surface of said human body such that light from said light source reaches said surface within the area enclosed by said cell.

17. Apparatus according to claim 16 wherein said measuring acoustic cell is suitable for detecting said resonant acoustic oscillations.

18. Apparatus according to claim 1 wherein said detector of said resonant acoustic oscillations is a piezoelectric crystal.

19. Apparatus according to claim 1 wherein said detector of said resonant acoustic oscillations is an optical fiber sensor.

20. Apparatus according to claim 1 wherein said detector of said resonant acoustic oscillations is a laser interferometer.

21. A method of determining a concentration of an interest component in a human body comprising the steps of:

irradiating a surface of said human body having said interest component with a light pulse-train comprising equidistant short pulses having variable duration, frequency, number, and power sufficient to excite resonant acoustic oscillations in said human body;

detecting said resonant/acoustic oscillations;

generating as electrical signal representative of the amplitude and the resonant frequency said resonant acoustic oscillations; and determining the concentration of said interest component in said human body in response to said electrical signal.

22. A method according to claim 21 wherein said irradiating step comprises a light beam having a predetermined wavelength for exciting of said resonant acoustic, oscillations in said human body due to absorption of light by said interest component and subsequent adiabatic temperature rise in a testing area of said human body.

23. A method according to claim 21 and further comprising tuning said wavelength to an absorption band of said, interest component sufficient to excite resonant acoustic-oscillations in said human body.

* * * * *